United States Patent [19]

Itagaki et al.

[11] Patent Number: 5,126,467

[45] Date of Patent: Jun. 30, 1992

[54] MODIFIER FOR COMPOSITE MATERIALS

[75] Inventors: Akinari Itagaki, Annaka; Hideyoshi Yanagisawa, Gunma; Masaaki Yamaya; Masayuki Takahashi, both of Annaka; Hiroshi Yoshioka, Tokyo, all of Japan

[73] Assignee: Shin-Etsu Chemical Co., Ltd., Tokyo, Japan

[21] Appl. No.: 589,025

[22] Filed: Sep. 27, 1990

[30] Foreign Application Priority Data

Sep. 28, 1989 [JP] Japan .................................. 1-252612

[51] Int. Cl.$^5$ .................................................. C07F 7/10
[52] U.S. Cl. ..................................... 556/413; 428/290; 428/375; 428/409; 428/429
[58] Field of Search ................ 556/413; 428/290, 375, 428/409, 429

[56] References Cited

U.S. PATENT DOCUMENTS

| 4,806,667 | 2/1989 | Böshagen et al. | 556/413 X |
| 4,921,988 | 5/1990 | Takatsuma et al. | 556/413 |
| 4,956,484 | 9/1990 | Gementi et al. | 556/413 X |

*Primary Examiner*—Arthur G. Prescott
*Attorney, Agent, or Firm*—Birch, Stewart, Kolasch & Birch

[57] ABSTRACT

Amino group-containing silicon compounds having at least two aromatic rings and hydrochlorides thereof are effective modifiers for composite materials for improving soldering heat resistance and heat shock resistance.

8 Claims, No Drawings

MODIFIER FOR COMPOSITE MATERIALS

This invention relates to modifiers for composite materials, and more particularly, to modifiers for use with composite materials comprising a matrix material such as glass fibers and mica bound with a resin for improving soldering heat resistance and heat shock resistance.

BACKGROUND OF THE INVENTION

Composite materials have been widely used in a variety of applications. Typical composite materials are based on a matrix in the form of a glass fiber preform such as glass cloth, glass tape, glass mat and glass paper or a mica preform which is bound with a resin binder such as epoxy, phenol, polyimide and polyamide resins. Among these, those composite materials having a matrix bound with an epoxy or polyimide resin are often used as printed circuit board laminates which are required to have high heat resistance because the laminates are dipped in a molten solder bath in a wiring step. With the recent advance of the technology, printed circuit board laminates are required to be thinner and more resistant to soldering heat.

One well-known prior art attempt for improving various properties of such laminates including mechanical strength, electrical properties, water and boiling water resistance, and chemical resistance is a pretreatment of a matrix with a silane coupling agent such as γ-aminopropyltriethoxysilane, β-aminoethyl-γ-aminopropyltrimethoxysilane, and γ-glycidoxy. propyltrimethoxysilane to improve bonding properties prior to treatment with a resin binder. The pretreatment with a silane coupling agent, however, cannot fully meet the requirement because substantial curing strains are induced at the interface between the silane coupling agent-treated matrix and the resin binder, which are undesirable for soldering heat resistance.

Some solutions to this problem are known in the art, for example, from Japanese Patent Publication No. 20609/1973 disclosing treatment with a hydrochloride of a silane compound of the formula:

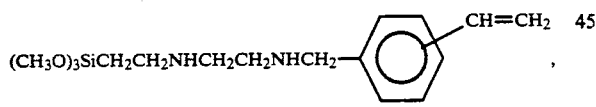

Japanese Patent Publication No. 41771/1982 disclosing treatment with an aniline-substituted silane compound, and Japanese Patent Application Kokai No. 48832/1989 disclosing treatment with a silane compound of the formula:

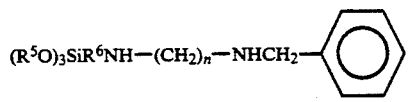

wherein $R^5$ is a methyl or ethyl group, $R^6$ is a divalent hydrocarbon group having 1 to 6 carbon atoms, and n is an integer of 4 to 8. However, laminates pretreated with these compounds are less resistant against blistering in thin film form.

The printed circuit board laminates have the problem that when dipped in molten solder, differential stresses due to the difference in coefficient of thermal expansion between the matrix and the binder resin, and in some cases, between the composite material and a copper cladding bonded to the surface for circuit wiring can break the bond therebetween. Therefore, it is desired for these products to improve heat shock resistance as well as soldering heat resistance.

SUMMARY OF THE INVENTION

Therefore, an object of the present invention is to provide a modifier for effectively improving the soldering heat resistance and heat shock resistance of composite materials for use as laminates. The modifier of the invention allows the composite material to form a thin layer exhibiting good soldering heat resistance and heat shock resistance as a laminate ply.

According to the present invention, there is provided a modifier for composite materials comprising an amino group containing silicon compound of the general formula:

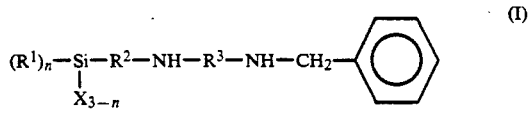

wherein $R^1$ is a monovalent hydrocarbon group having 1 or 2 carbon atoms, $R^2$ is a divalent aromatic ring-containing hydrocarbon group having 6 to 10 carbon atoms, $R^3$ is a divalent hydrocarbon group having 2 to 8 carbon atoms, X is an alkoxy group having 1 or 2 carbon atoms, and n is a number equal to 0, 1 or 2, or a hydrochloride salt thereof.

We have found that significant soldering heat resistance and heat shock resistance can be imparted to composite materials through the use of an amino group-containing alkoxysilane having at least two aromatic rings per molecule, that is, the aromatic ring introduced into $R^2$ substituent and the aromatic ring of a benzyl group

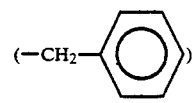

as seen from formula (I). A matrix such as a glass fiber or mica form is pretreated with a liquid having the above-defined amino group-containing silicon compound or hydrochloride thereof blended as an active ingredient and then bound with an epoxy or polyimide resin to form a composite material in which the matrix and the resin binder are firmly bonded to each other without inducing a curing strain and the bonding interface is soft and resistant against water. As to the thin layer form, this composite material can be formed into a laminate ply having excellent soldering heat resistance and heat shock resistance.

DETAILED DESCRIPTION OF THE INVENTION

The composite materials to which the modifier of the invention can be applied for improving their properties include a wide variety of composite materials comprising a matrix bound with a resin binder. Examples of the matrix include glass fiber forms or articles such as nonwoven glass mat and glass paper prepared from glass strands which are bundles of glass filaments spun from alkali glass, alkali-free glass, low induction glass, high modulus glass and electrical E glass, glass cloth woven from glass yarns, and glass tape, and mica forms or articles such as soft and hard mica masses prepared from mica flakes. Examples of the resin binder include epoxy resins (e.g., bisphenol A epoxy resins, phenol novolak epoxy resins, and cresol novolak epoxy resins), polyamide, polyimide, polyester, polyphenylene ether, phenol resins, nylon and other well-known binder resins.

The modifier of the invention is based on an amino group-containing silicon compound of the general formula:

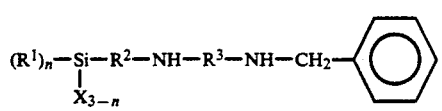
(I)

or a hydrochloride salt thereof.

In formula (I), substituent $R^1$ is a monovalent hydrocarbon group having 1 or 2 carbon atoms, such as $CH_3$ and $CH_3CH_2$;

substituent $R^2$ is a divalent hydrocarbon group containing an aromatic ring and having 6 to 10 carbon atoms, for example,

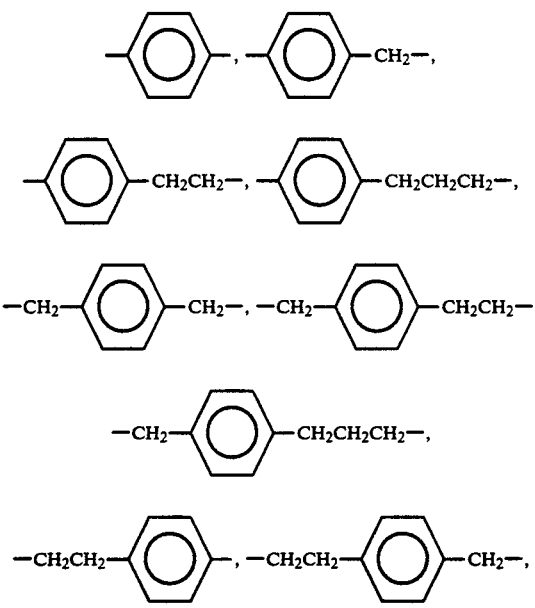

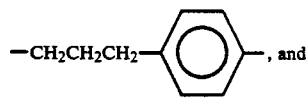

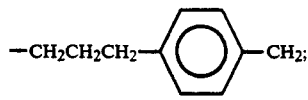

substituent $R^3$ is a divalent hydrocarbon group having 2 to 8 carbon atoms, for example, $-CH_2CH_2-$, $-(CH_2)_3-$, $(CH_2)_4-$,

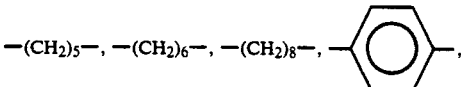

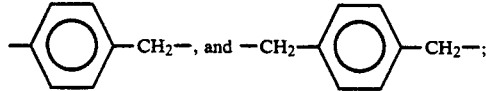

substituent X is an alkoxy group having 1 or 2 carbon atoms, for example, $CH_3O$ and $CH_3CH_2O$, and letter n is a number equal to 0, 1 or 2.

If the aromatic hydrocarbon group represented by $R^2$ has more than 10 carbon atoms, it becomes difficult to isolate precursors of the compound of formula (I), for example,

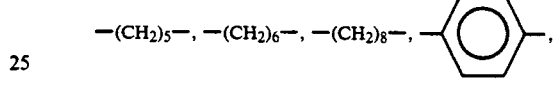

resulting in undesirable contamination with impurities. Similar contamination occurs if the hydrocarbon group represented by $R^3$ has more than 8 carbon atoms, whereas the starting materials corresponding to $R^3$ with less than 2 carbon atoms are undesirable because they are expensive and difficult to handle.

Several illustrative, non-limiting examples of the amino group-containing silicon compound of formula (I) are given below.

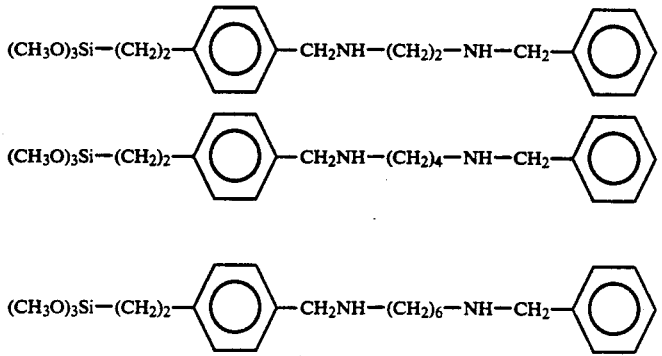

-continued

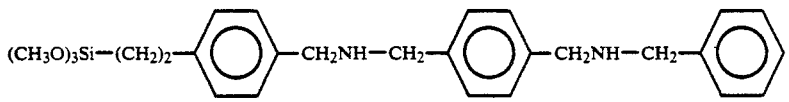

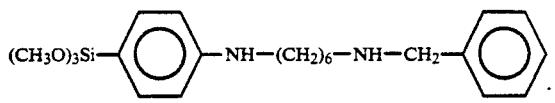

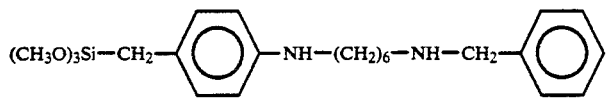

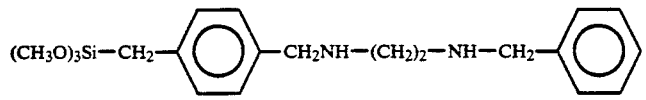

The amino group containing silicon compounds of formula (I) may be prepared, for example, by reacting a silane compound of the general formula:

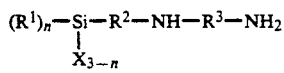

wherein $R^1$, $R^2$, $R^3$ and X, and n are as defined above with the compound of the formula:

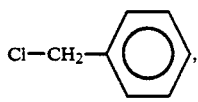

or by reacting a silane compound of the general formula:

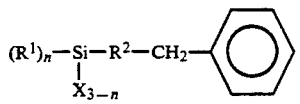

wherein $R^1$, $R^2$, X and n are as defined above with a compound of the formula:

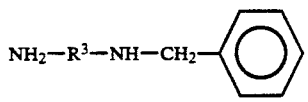

wherein $R^3$ is as defined above.

These reactions are preferably effected in a solvent system. The solvent used herein is preferably selected from alcohols such as methanol, ethanol and butanol although aromatic and aliphatic hydrocarbon solvents are also useful. The reaction conditions are not particularly limited although it is preferred to heat at about 50° to about 150° C. for about 2 to about 12 hours. A hydrochloride salt is normally obtained although an amino group-containing silane compound rather than the hydrochloride is obtained by scavenging hydrogen chloride with sodium alcoholates or tertiary amines such as pyridine and triethylamine during reaction.

The modifier of the invention is obtained by blending the amino group-containing silane compound of formula (I) or its hydrochloride as an active ingredient, preferably by diluting the compound or hydrochloride with a suitable solvent to form a liquid for treatment. The preferred solvents used herein are water and aqueous solutions of 0.5 to 2% by weight acetic acid while lower alcohols such as methanol and ethanol may be added thereto. The liquid for treatment is preferably prepared to such a concentration that it contains 0.2 to 2% by weight, more preferably 0.5 to 1% by weight of the amino group-containing silane compound.

The liquid for treatment may optionally contain dyes, pigments, anti-static agents, lubricants, and silicon compounds other than formula (I).

Composite materials are treated with the modifier of the invention, typically by dipping a matrix such as a glass fiber or mica form in the above prepared liquid for treatment. If desired, the pick-up of the aqueous solution by the reinforcing material can be controlled by means of a squeeze roll or the like. It is also possible to spray the liquid for treatment to mica sheets. The thus treated matrix is dried preferably by heating at about 60° C. to about 120° C. for about 5 to about 30 minutes to thereby remove the solvent and at the same time, condense and bond the silanol group of the silane compound to the matrix surface.

The matrix pretreated with the modifier of the invention is then treated with a resin binder such as an epoxy or polyimide resin to form a composite material in which the matrix is firmly bonded to the resin binder with the bonding interface being soft, resistant against water, and free of a curing strain. The composite material can be formed into a thin laminate layer having excellent soldering heat resistance and heat shock resistance.

There has been described a modifier which is effective in improving the soldering heat resistance and heat shock resistance of composite materials. The composite materials treated with the present modifier can be formed into thin layers from which laminates having excellent soldering heat resistance and heat shock resistance can be prepared. Therefore, the treated composite materials are effectively utilized as printed circuit board laminates which are desired to be thin.

EXAMPLE

In order that those skilled in the art better understand the present invention, examples of the invention are given below together with comparative examples by way of illustration and not by way of limitation. Synthesis of an amino group-containing silicon compound of formula (I) is also illustrated. All parts are parts by weight.

The following tests were carried out to evaluate the products.

[Boiling water absorption (%)]

According to the test method of JIS C-6481, a sample of 50×50 mm was cut out from a copper clad laminate from which the copper cladding had been removed by etching, kept in boiling water for 4 to 16 hours, and measured for water absorption.

[Soldering heat resistance]

The sample which has subjected to the boiling water absorption test was placed on a solder bath at 260° C. for 30 seconds or at 290° C. for 30 seconds. The area of the sample where blisters occurred was calculated as blister area (%).

[Heat shock resistance]

A copper clad laminate was dipped in liquid nitrogen for one minute and immediately thereafter dipped in a solder bath at 290° C. for 30 seconds. The copper cladding was then removed by etching, for allowing observation of damages to the laminate. The sample was evaluated to the following four ratings.

E: Excellent
G: A few defective spots occurred.
F: Defective spots occurred.
P: Overall damages with delamination.

SYNTHESIS 1

A 1-liter separable flask equipped with a thermometer, condenser, and dropping funnel was charged with 354 grams (1.0 mol) of the silane of the formula:

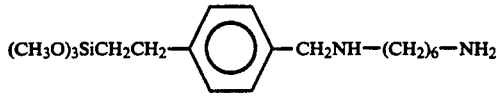

and 480.5 grams (15.02 mol) of methanol and heated to 60° C. Then 126.6 grams (1.0 mol) of benzyl chloride was added dropwise at such a rate to keep the contents at 60° to 70° C. At the end of addition, the reaction mixture was stirred for 4 hours with methanol refluxing. Completion of reaction was acknowledged by measurement of hydrogen chloride quantity.

There was obtained an amino group-containing silicon compound of the following structure having a viscosity of 6.12 centistokes at 25° C. and a specific gravity of 0.929.

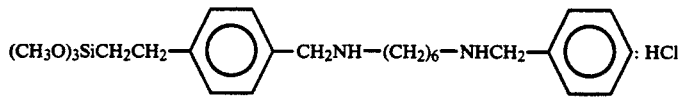

EXAMPLE 1

A glass cloth, WE 18K107B (manufactured by Nitto Boseki K.K.) whose surface had been cleaned by heat cleaning was dipped in a liquid for treatment which was prepared by dissolving the amino group-containing silicon compound hydrochloride of the formula:

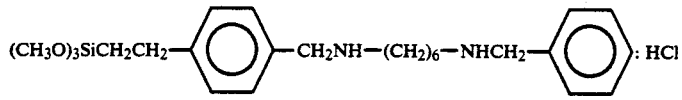

(obtained in Synthesis 1, to be referred to as Silane I) in a 1 wt % acetic acid aqueous solution to a concentration of 5 gram/liter, passed between squeeze rolls, and then dried at 110° C. for 15 minutes.

Separately, a resin varnish was prepared by blending 80 parts of a bisphenol type epoxy resin, Epicoat 1001 (manufactured by Yuka Shell Epoxy K.K.), 20 parts by weight of a novolak type epoxy resin, Epicoat 154 (manufactured by Yuka Shell Epoxy K.K.), 4.0 parts of dicyandiamide, 0.2 parts of benzyldimethylamine, 20 parts of methyl ethyl ketone, and 45 parts of methyl cellosolve according to the NEMA Standard's G.10 formulation. The silane treated glass cloth was impregnated with the resin varnish. Precuring at 160° C. for 6 minutes resulted in a B stage prepreg. A double side copper clad epoxy laminate was prepared by stacking 8 plies of such prepreg and applying copper claddings on opposite sides of the stack, followed by press molding at 170° C. and 35 kg/cm² for 60 minutes.

EXAMPLES 2-3 AND COMPARATIVE EXAMPLES 1-4

Treating solutions were prepared as in Example 1 except that the following silane compounds or hydrochlorides designated Silanes II to VII which were obtained as in Synthesis 1 were used instead of Silane I. For Silanes VI and V, pure water was used instead of the acetic acid solution because of their solubility in water. By following the procedures of Example 1, glass cloths were treated with these solutions, and double side copper clad epoxy laminates were prepared therefrom.

Silane II:

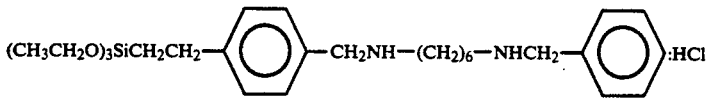

Silane III:

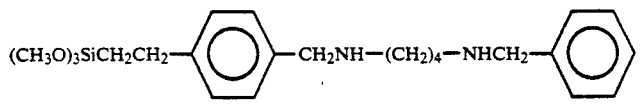

Silane IV: (comparison)

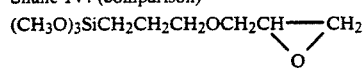

Silane V: (comparison)

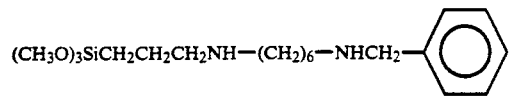

Silane VI: (comparison)

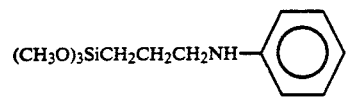

Silane VII: (comparison)

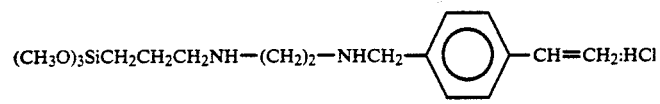

The thus prepared double side copper clad epoxy laminates were examined for boiling water absorption, soldering heat resistance (260° C./30 seconds), and heat shock resistance according to the above-mentioned test procedures. The results are shown in Table 1.

EXAMPLES 4–6 AND COMPARATIVE EXAMPLES 5–8

Treating solutions were prepared as in Example 1 except that the following silane compounds or hydro-chlorides designated Silanes VIII to X which were obtained as in Synthesis 1 were used instead of Silane I.

TABLE 1

| Example | Silane | Laminate's glass content (%) | Water absorption (%) after boiling for | | | Soldering heat resistance Blister area (%) after boiling for | | | Heat shock |
|---|---|---|---|---|---|---|---|---|---|
| | | | 4 hr. | 8 hr. | 14 hr. | 4 hr. | 8 hr. | 14 hr. | |
| E1 | I | 59.8 | 0.62 | 0.88 | 1.14 | 0 | 1.6 | 10.9 | Good |
| E2 | II | 60.1 | 0.63 | 0.89 | 1.16 | 0 | 2.3 | 13.5 | Excellent. |
| E3 | III | 60.4 | 0.62 | 0.90 | 1.15 | 0 | 3.6 | 16.2 | Excellent |
| CE1 | IV | 60.0 | 0.76 | 1.15 | 1.50 | 25.3 | 64.8 | >80 | Poor |
| CE2 | V | 59.8 | 0.64 | 0.92 | 1.19 | 0 | 7.6 | 24.0 | Good |
| CE3 | VI | 60.2 | 0.65 | 0.95 | 1.17 | 0 | 8.6 | 30.6 | Fair |
| CE4 | VII | 60.3 | 0.63 | 0.85 | 1.16 | 0 | 5.9 | 27.0 | Fair |

As seen from Table 1, the laminates prepared through treatment with the present modifiers show excellent soldering heat resistance and heat shock resistance.

Silane VIII:

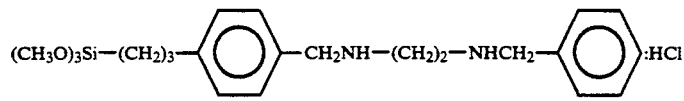

Silane IX:

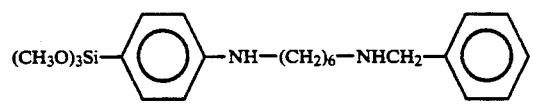

Silane X:

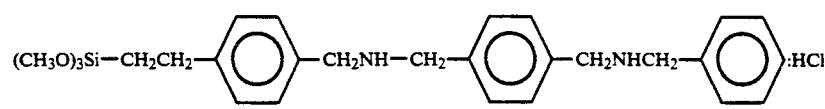

Glass cloths were respectively treated with the solutions of Silanes VIII to X and the solutions of Silanes V to VII as in Example 1.

Separately, a resin varnish was prepared by blending 100 parts of a brominated epoxy resin, Epicoat 5046-B-80 (manufactured by Yuka Shell Epoxy K.K.), 20 parts by weight of a novolak type epoxy resin, Epicoat 154 (manufactured by Yuka Shell Epoxy K.K.), 4 parts of dicyandiamide, 0.2 parts of 2-ethyl-4-methylimidazole, 15 parts of methyl ethyl ketone, and 30 parts of dimethylformamide according to the NEMA Standard's FR-4 formulation. The silane treated glass cloths were impregnated with the resin varnish to produce prepregs. Thereafter, double side copper clad epoxy laminates were prepared from the prepregs as in Example 1.

The thus prepared double side copper clad epoxy laminates were examined for boiling water absorption, soldering heat resistance (260° C./30 seconds), and heat shock resistance according to the above-mentioned test procedures. The results are shown in Table 2.

TABLE 2

| Example | Silane | Laminate's glass content (%) | Water absorption (%) after boiling for 8 hr. | Water absorption (%) after boiling for 12 hr. | Soldering heat resistance Blister area (%) after boiling for 8 hr. | Soldering heat resistance Blister area (%) after boiling for 12 hr. | Heat shock |
|---|---|---|---|---|---|---|---|
| E4 | VIII | 60.2 | 0.56 | 0.69 | 0 | 5.2 | Good |
| E5 | IX | 60.5 | 0.58 | 0.71 | 0 | 3.9 | Excellent |
| E6 | X | 60.1 | 0.60 | 0.73 | 0 | 2.5 | Good |
| CE5 | IV | 59.8 | 0.92 | 1.32 | 34.4 | 65.3 | Poor |
| CE6 | V | 59.7 | 0.54 | 0.72 | 1.3 | 8.1 | Fair |
| CE7 | VI | 60.1 | 0.65 | 0.82 | 12.3 | 22.3 | Poor |
| CE8 | VII | 59.8 | 0.54 | 0.68 | 6.5 | 10.4 | Fair |

The results reported in Table 2 are equivalent to those in Table 1, indicating that the present modifiers are effective in improving the soldering heat resistance and heat shock resistance of a composite material.

Although some preferred embodiments have been described, many modifications and variations may be made thereto in the light of the above teachings. It is therefore to be understood that within the scope of the appended claims, the invention may be practiced otherwise than as specifically described.

We claim:

1. A modifier for composite materials comprising an amino group-containing silicon compound of the general formula:

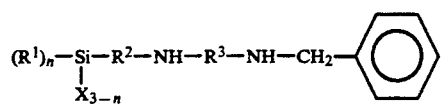

(I)

wherein $R^1$ is a monovalent hydrocarbon group having 1 or 2 carbon atoms, $R^2$ is a divalent aromatic ring-containing hydrocarbon group having 6 to 10 carbon atoms, $R^3$ is a divalent hydrocarbon group having 2 to 8 carbon atoms, X is an alkoxy group having 1 or 2 carbon atoms, and n is a number equal to 0, 1 or 2, or a hydrochloride thereof.

2. The modifier according to claim 1, wherein the compound of formula (I) is in the form of a solution which is suitable for treating the matrix of a composite material.

3. The modifier according to claim 2, wherein the solution contains 0.2 to 2% by weight of the compound of formula (I).

4. A composite material comprising a matrix selected from the group consisting of glass fiber forms and mica forms and a resin binder binding said matrix, wherein said matrix has applied thereto a modifier comprising an amino group-containing silicon compound of the general formula:

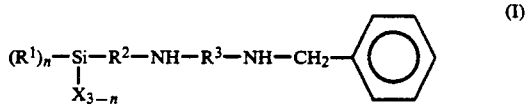

(I)

wherein $R^1$ is a monovalent hydrocarbon group having 1 or 2 carbon atoms, $R^2$ is a divalent aromatic ring-containing hydrocarbon group having 6 to 10 carbon atoms, $R^3$ is a divalent hydrocarbon group having 2 to 8 carbon atoms, X is an alkoxy group having 1 or 2 carbon atoms, and n is a number equal to 0, 1 or 2, or a hydrochloride thereof.

5. The modifier of claim 1, wherein $R^2$ is selected from the group consisting of

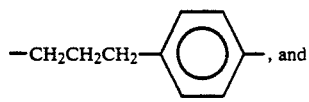, and
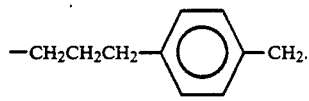
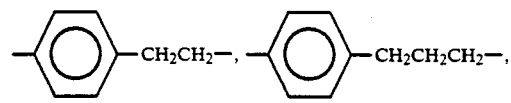
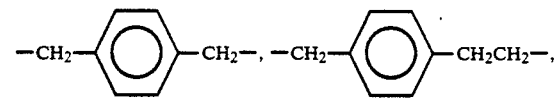
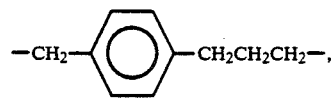
6. The modifier of claim 1, wherein said modifier is selected from the group consisting of
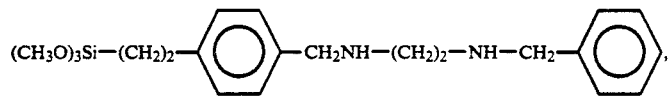
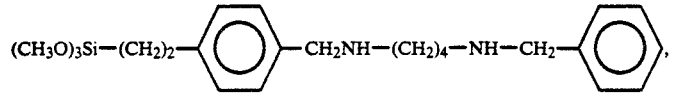
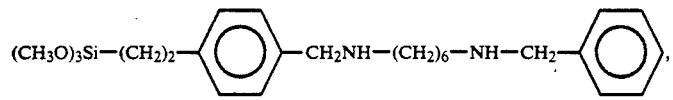
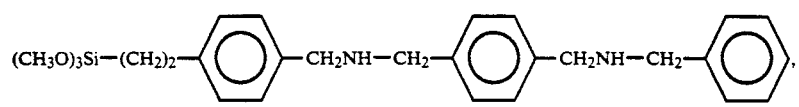
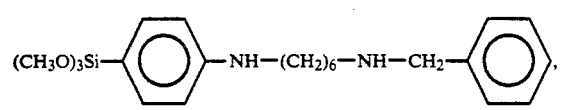
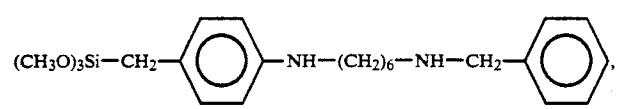
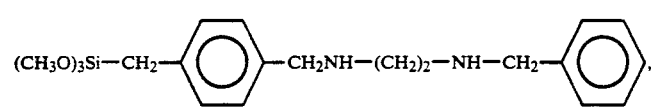
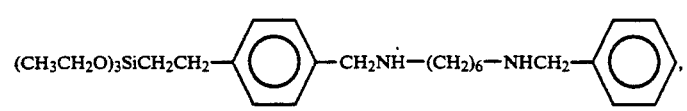
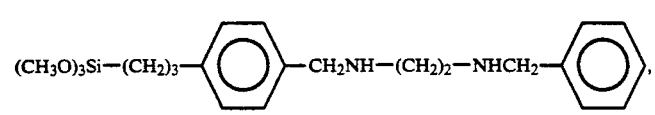
and hydrochlorides thereof.
7. The composite material according to claim 4, wherein $R^2$ is selected from the group consisting of
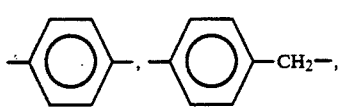
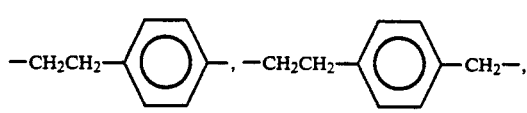

-continued
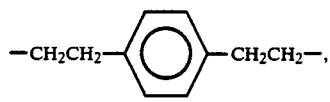
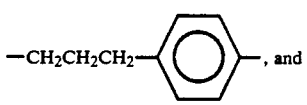
-continued
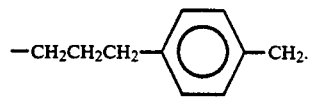
8. The composite material according to claim 4, wherein said modifier is selected from the group consisting of
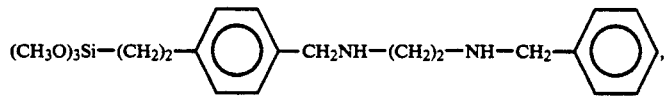
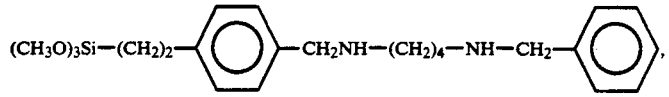
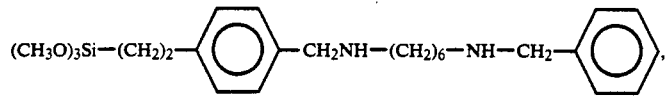
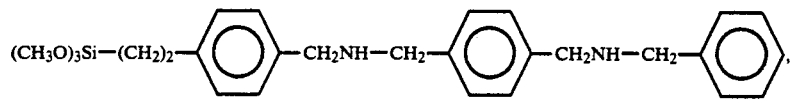
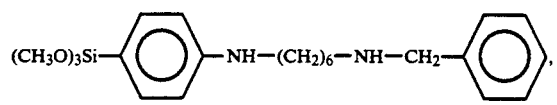
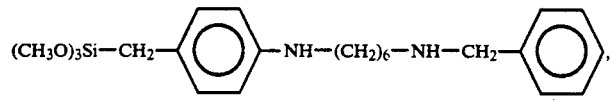
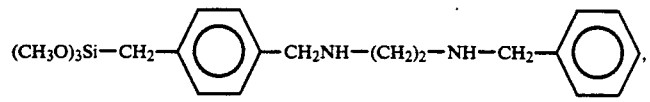
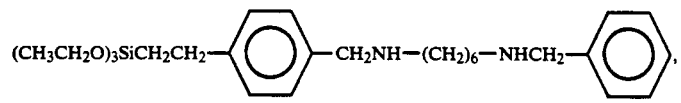
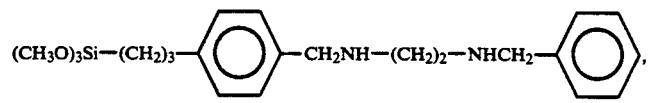
and hydrochlorides thereof.
* * * * *